US010342975B2

United States Patent
Ridler et al.

(10) Patent No.: US 10,342,975 B2
(45) Date of Patent: Jul. 9, 2019

(54) MICRO-CHARGE STIMULATION

(71) Applicant: Cochlear Limited, Macquarie University, NSW (AU)

(72) Inventors: Oliver John Ridler, Sydney (AU); Paul Michael Carter, West Pennant Hills (AU)

(73) Assignee: COCHLEAR LIMITED, Macquarie University (AU)

( * ) Notice: Subject to any disclaimer, the term of this patent is extended or adjusted under 35 U.S.C. 154(b) by 0 days.

(21) Appl. No.: 15/158,120

(22) Filed: May 18, 2016

(65) Prior Publication Data

US 2017/0072196 A1  Mar. 16, 2017

Related U.S. Application Data

(60) Provisional application No. 62/217,994, filed on Sep. 14, 2015.

(51) Int. Cl.
  *A61N 1/36* (2006.01)
(52) U.S. Cl.
  CPC ..... *A61N 1/36036* (2017.08); *A61N 1/36038* (2017.08)
(58) Field of Classification Search
  CPC ...... A61N 1/025; A61N 1/0541; A61N 1/323; A61N 1/36032; A61N 1/36125; A61N 1/36164; A61N 1/36167; A61N 1/36171; A61N 1/36175; A61N 1/36178; A61N 1/3628; A61N 1/378; A61N 1/3782
  See application file for complete search history.

(56) References Cited

U.S. PATENT DOCUMENTS

| 4,947,844 | A | * | 8/1990 | McDermott | A61B 5/12 607/57 |
| 5,109,847 | A | * | 5/1992 | Liss | A61N 1/36021 607/46 |
| 5,385,575 | A | * | 1/1995 | Adams | A61N 1/3956 607/15 |
| 5,534,015 | A | * | 7/1996 | Kroll | A61N 1/3956 607/5 |
| 5,601,617 | A | * | 2/1997 | Loeb | A61N 1/36036 607/56 |
| 5,817,138 | A | * | 10/1998 | Suzuki | A61N 1/323 607/67 |
| 5,991,663 | A | | 11/1999 | Irlicht et al. | |
| 6,259,951 | B1 | | 7/2001 | Kuzma et al. | |
| 6,535,767 | B1 | * | 3/2003 | Kronberg | A61N 1/326 607/51 |
| 7,054,686 | B2 | * | 5/2006 | MacDonald | A61N 1/368 607/9 |

(Continued)

OTHER PUBLICATIONS

Definition of "micro". Merriam-Webster.com. Accessed Jun. 9, 2018.*

(Continued)

*Primary Examiner* — Eugene T Wu
(74) *Attorney, Agent, or Firm* — Edell, Shapiro & Finnan, LLC (57) ABSTRACT

Presented herein are stimulation techniques for implantable tissue-stimulating systems. The stimulation techniques generate and deliver sets of micro-charge pulses to a recipient. The micro-charge pulses within a set collectively cause the firing of a recipient's nerve cell(s).

21 Claims, 9 Drawing Sheets

(56) References Cited

U.S. PATENT DOCUMENTS

| | | | | |
|---|---|---|---|---|
| 7,191,014 | B2* | 3/2007 | Kobayashi | A61N 1/36014 607/72 |
| 7,333,858 | B2* | 2/2008 | Killian | A61N 1/36036 607/55 |
| 8,224,453 | B2* | 7/2012 | De Ridder | A61N 1/36071 607/117 |
| 8,364,273 | B2* | 1/2013 | De Ridder | A61N 1/36071 607/45 |
| 8,401,655 | B2* | 3/2013 | De Ridder | A61N 1/0531 607/45 |
| 8,612,018 | B2* | 12/2013 | Gillbe | A61N 1/0551 607/72 |
| 9,283,384 | B2* | 3/2016 | Turumaki | A61N 1/36003 |
| 9,289,610 | B2* | 3/2016 | Parramon | A61N 1/0551 |
| 2002/0012438 | A1 | 1/2002 | Leysieffer et al. | |
| 2008/0172108 | A1 | 7/2008 | Lierhofer et al. | |
| 2014/0107730 | A1 | 4/2014 | Lierhofer | |

OTHER PUBLICATIONS

Inntemational Search Report and Written Opinion in counterpart International Application No. PCT/IB2016/055445, dated Nov. 21, 2016, 14 pages.

Maysam Ghovanloo "Switched-Capacitor Based Implantable Low-Power Wireless Microstimulating Systems," IEEE Xplore, Jun. 2006, pp. 2197-2200.

Orlando Lazaro, et al., "Switched-Capacitor Charging System for an Implantable Neurological Stimulator", Feb. 6, 2009, pp. 1-4.

Jose Vidal Jr., et al., "Towards a Switched-Capacitor Based Stimulator for Efficient Deep-Brain Stimulation", IEEE Eng Med Biol Soc. 2010, 2010, pp. 2927-2930.

Hyung-Min Lee, et al., "A Power-Efficient Switched-Capacitor Stimulating System for Electrical/Optical Deep-Brain Stimulation," IEEE International Solid-State Circuits Conference, 2014, pp. 414-416.

\* cited by examiner

MICRO-CHARGE STIMULATION

CROSS REFERENCE TO RELATED APPLICATIONS

This application claims priority to U.S. Provisional Application No. 62/217,994 entitled "Micro-Charge Stimulation," filed Sep. 14, 2015, the content of which is hereby incorporated by reference herein.

BACKGROUND

Field of the Invention

The present invention relates generally to implantable tissue-stimulating systems.

Related Art

Hearing loss, which may be due to many different causes, is generally of two types, conductive and/or sensorineural. Conductive hearing loss occurs when the normal mechanical pathways of the outer and/or middle ear are impeded, for example, by damage to the ossicular chain or ear canal. Sensorineural hearing loss occurs when there is damage to the inner ear, or to the nerve pathways from the inner ear to the brain.

Individuals who suffer from conductive hearing loss typically have some form of residual hearing because the hair cells in the cochlea are undamaged. As such, individuals suffering from conductive hearing loss typically receive an auditory prosthesis that generates motion of the cochlea fluid. Such auditory prostheses include, for example, acoustic hearing aids, bone conduction devices, and direct acoustic stimulators.

In many people who are profoundly deaf, however, the reason for their deafness is sensorineural hearing loss. Those suffering from some forms of sensorineural hearing loss are unable to derive suitable benefit from auditory prostheses that generate mechanical motion of the cochlea fluid. Such individuals can benefit from implantable auditory prostheses that stimulate nerve cells of the recipient's auditory system in other ways (e.g., electrical, optical and the like). Cochlear implants are often proposed when the sensorineural hearing loss is due to the absence or destruction of the cochlea hair cells, which transduce acoustic signals into nerve impulses. An auditory brainstem stimulator is another type of stimulating auditory prosthesis that might also be proposed when a recipient experiences sensorineural hearing loss due to damage to the auditory nerve.

SUMMARY

In one aspect, a method is provided. The method comprises receiving one or more signals at an implantable tissue-stimulating system implanted in a recipient; and generating, based on the one or more signals, a set of micro-charge pulses that, when delivered in sequence to a group of nerve cells of the recipient, collectively evoke perception of at least a portion of the signals.

In another aspect, a stimulating auditory system is provided. The stimulating auditory system comprises at least one sound input element configured to receive one or more sound signals; a sound processor configured to generate processed sound signals representative of the one or more sound signals; and an implantable stimulator unit configured to generate, based on the processed sound signals, a set of micro-charge pulses for delivery to nerve cells of a recipient, wherein the set of micro-charge pulses is configured to activate a group of nerve cells to evoke perception of a portion of the processed sound signals.

In another aspect, a method is provided. The method comprises: generating, at a sound processor of a stimulating auditory system, processed sound signals; generating, at a micro-charge pulse injection circuit, a plurality of micro-charge pulses; and delivering, via a switching circuit, the plurality of micro-charge pulses to a group of nerve cells of the recipient in sequence so as to evoke perception of at least a portion of the processed sound signals.

BRIEF DESCRIPTION OF THE DRAWINGS

Embodiments of the present invention are described herein in conjunction with the accompanying drawings, in which.

DETAILED DESCRIPTION

Embodiments of the present invention are generally directed to stimulation techniques that generate and deliver discrete sets/sequences of micro-charge pulses to a recipient. The micro-charge pulses within a set collectively (i.e., in aggregate) cause the firing of a recipient's nerve cell(s) to evoke perception of, for example, a portion of a sound signal.

There are several types of implantable tissue-stimulating systems that operate by delivering stimulation to a recipient so as to compensate for a deficiency in the recipient's nerves, tissue, etc. Merely for ease of illustration, the techniques presented herein are primarily described with reference to one type of implantable tissue-stimulating system, namely a cochlear implant system. However, it is to be appreciated that the techniques presented herein may be used in other stimulating auditory systems, such as auditory brainstem stimulator systems, or in other implantable tissue-stimulating systems that include, for example, pacemakers, defibrillators, functional electrical stimulation devices, pain relief stimulators, visual prostheses, other neural or neuromuscular stimulators, etc.

Figure 1A:
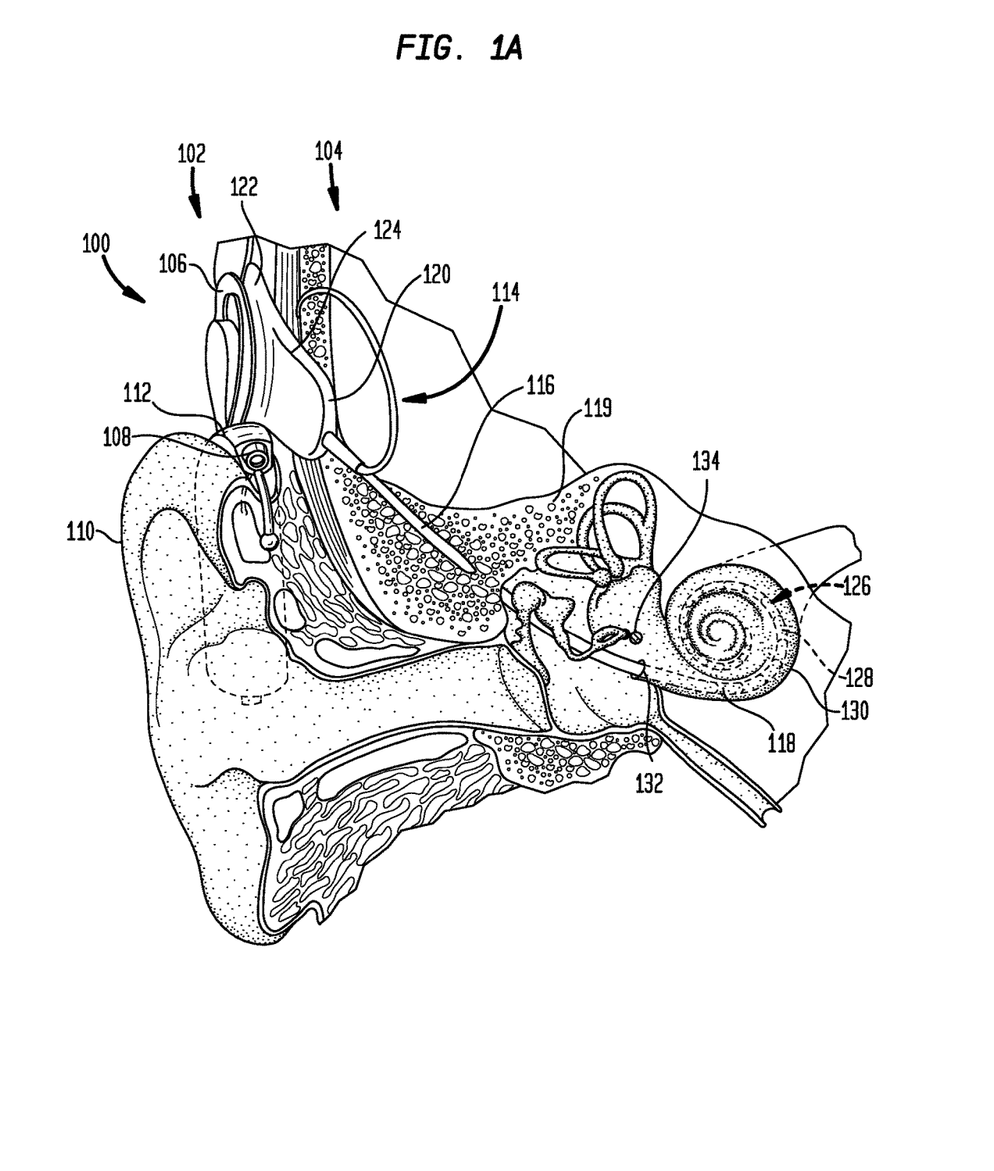
FIG. 1A is a schematic diagram illustrating a cochlear implant system in accordance with embodiments presented herein.

FIG. 1A is schematic diagram of an exemplary cochlear implant system 100 configured to implement embodiments of the present invention. The cochlear implant system 100 comprises an external component 102 and an internal/implantable component 104. In this example, the implantable component 104 is a cochlear implant.

The external component 102 is directly or indirectly attached to the body of the recipient and typically comprises an external coil 106 and, generally, a magnet (not shown in FIG. 1A) fixed relative to the external coil 106. The external component 102 also comprises one or more sound input elements 108 (e.g., microphones, telecoils, etc.) for detecting/receiving sound signals, and a sound processing unit 112. The sound processing unit 112 includes, for example, a power source (not shown in FIG. 1A) and a sound processor (also not shown in FIG. 1A). The sound processor is configured to process electrical signals generated by a sound input element 108 that is positioned, in the depicted embodiment, by auricle 110 of the recipient. The sound processor provides the processed signals to external coil 106 via, for example, a cable (not shown in FIG. 1A).

The cochlear implant 104 comprises an implant body 114, a lead region 116, and an elongate intra-cochlear stimulating assembly 118. The implant body 114 comprises a stimulator unit 120, an internal/implantable coil 122, and an internal receiver/transceiver unit 124, sometimes referred to herein as transceiver unit 124. The transceiver unit 124 is connected to the implantable coil 122 and, generally, a magnet (not shown) fixed relative to the internal coil 122.

The magnets in the external component 102 and cochlear implant 104 facilitate the operational alignment of the external coil 106 with the implantable coil 122. The operational alignment of the coils enables the implantable coil 122 to transmit/receive power and data to/from the external coil 106. More specifically, in certain examples, external coil 106 transmits electrical signals (e.g., power and stimulation data) to implantable coil 122 via a radio frequency (RF) link. Implantable coil 122 is typically a wire antenna coil comprised of multiple turns of electrically insulated single-strand or multi-strand platinum or gold wire. The electrical insulation of implantable coil 122 is provided by a flexible molding (e.g., silicone molding). In use, transceiver unit 124 may be positioned in a recess of the temporal bone of the recipient. Various other types of energy transfer, such as infrared (IR), electromagnetic, capacitive and inductive transfer, may be used to transfer the power and/or data from an external device to a cochlear implant and, as such, FIG. 1A illustrates only one example arrangement.

Elongate stimulating assembly 118 is configured to be at least partially implanted in cochlea 130 and includes a plurality of longitudinally spaced intra-cochlear electrical stimulating contacts (electrical contacts) 128 that collectively form a contact array 126. Stimulating assembly 118 extends through an opening in the cochlea 130 (e.g., cochleostomy 132, the round window 134, etc.) and has a proximal end connected to stimulator unit 120 via lead region 116 that extends through mastoid bone 119. Lead region 116 couples the stimulating assembly 118 to implant body 114 and, more particularly, stimulator unit 120.

In general, the sound processor in sound processing unit 112 is configured to execute sound processing and coding to convert a detected sound into a coded signal that represents the detected sound signals. These encoded data are sometimes referred to herein as processed sound signals.

Figure 1B:
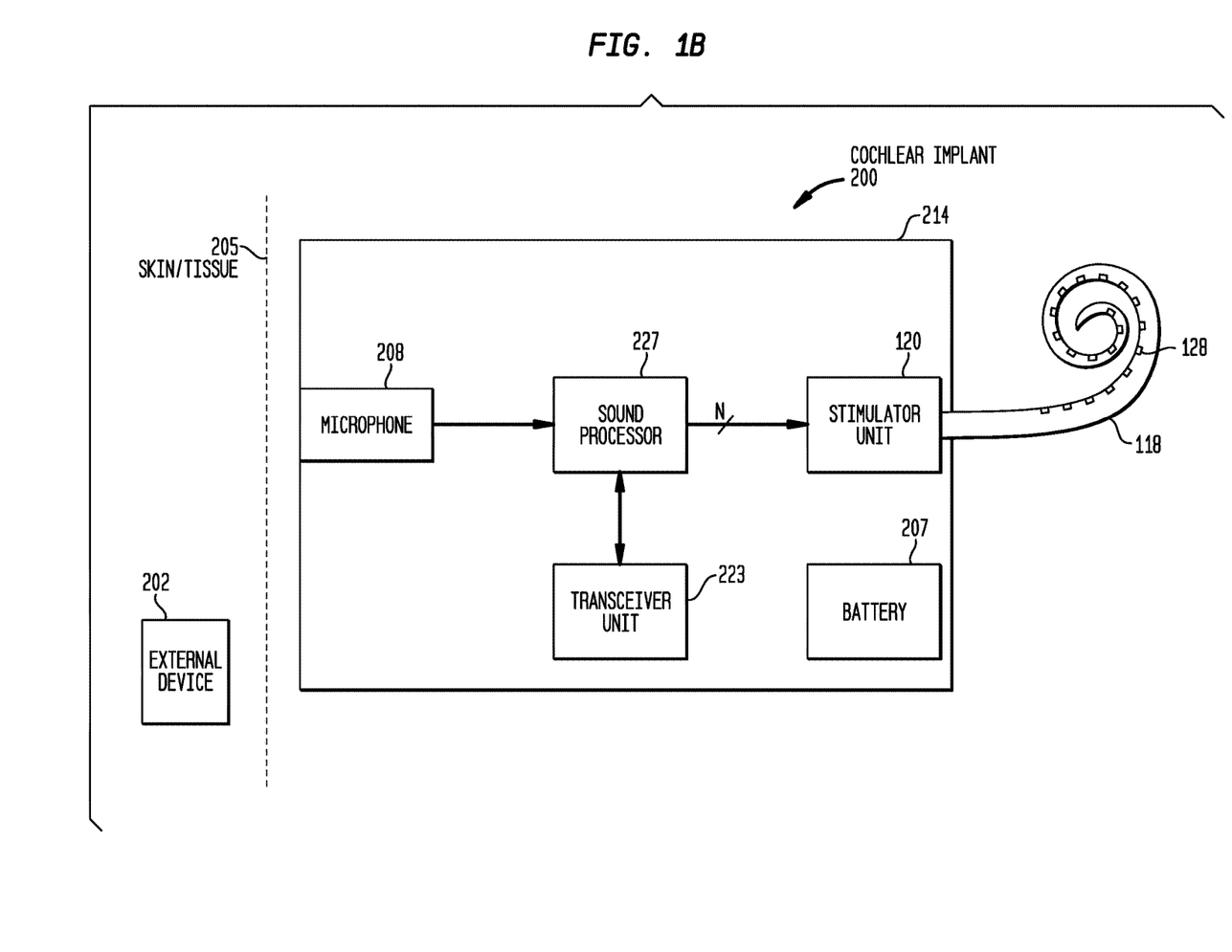
FIG. 1B is a block diagram of a totally implantable cochlear implant system in accordance with embodiments presented herein.

FIG. 1A illustrates an arrangement in which the cochlear implant system 100 includes an external component. However, it is to be appreciated that embodiments of the present invention may be implemented in cochlear implant systems having alternative arrangements. For example, 1B is a functional block diagram of an exemplary totally implantable cochlear implant system 200 configured to implement embodiments of the present invention. Since the cochlear implant system 200 is totally implantable, all components of cochlear implant system 200 are configured to be implanted under skin/tissue 205 of a recipient. Because all components of cochlear implant system 100 are implantable, cochlear implant system 200 operates, for at least a finite period of time, without the need of an external device. An external device 202 can be used to, for example, charge the internal power source (battery) 207. External device 202 may be a dedicated charger or a conventional cochlear implant sound processor.

Cochlear implant system 200 includes an implant body (main implantable component) 214 and an implantable microphone 208, an elongate intra-cochlear stimulating assembly 118 as described above with reference to FIG. 1A. The microphone 208 may be disposed in, or electrically connected to, the implant body 214. The implant body 214 further comprises an internal transceiver unit 223, a sound processor 227, a stimulator unit 120 as described with reference to FIG. 1A, the battery 207.

The sound processor 227 is configured to execute sound processing and coding to convert received/detected sound signals (e.g., received by microphone 208) into processed sound signals.

The transceiver unit 223 permits cochlear implant system 200 to receive and/or transmit signals to external device 202. For example, transceiver unit 223 may be configured to transcutaneously receive power and/or data from external device 202. However, as used herein, transceiver unit 223 refers to any collection of one or more implanted components which form part of a transcutaneous energy transfer system. Further, transceiver unit 223 includes any number of component(s) which receive and/or transmit data or power, such as, for example a coil for a magnetic inductive arrangement, an antenna for an alternative RF system, capacitive plates, or any other suitable arrangement. Various types of energy transfer, such as infrared (IR), electromagnetic, capacitive and inductive transfer, can be used to transfer the power and/or data from external device 202 to cochlear implant system 200.

As noted above, FIG. 1A illustrates an embodiment in which the external component 102 includes the sound processor. As such, in the illustrative arrangement of FIG. 1A, processed sound signals are provided to the implanted stimulator unit 120 via the RF link between the external coil 106 and the internal coil 122. However, in the embodiment of FIG. 1B, the sound processor 227 is implanted in the recipient. As such, in the embodiments of FIG. 1B, the processed sound signals do not traverse the RF link, but instead are provided directly to the stimulator unit 120.

Because the cochlea is tonotopically mapped, that is, partitioned into regions each responsive to stimulus signals in a particular frequency range, acoustic frequencies are allocated to one or more electrical contacts 128 of the stimulating assembly 118 that are positioned close to the region that would naturally be stimulated in normal (acoustic) hearing. As such, processing channels of the sound processor (i.e., specific frequency bands with their associated signal processing paths) are each mapped to a set of one or more stimulating contacts to stimulate a selected population of cochlea nerve cells, sometimes referred to as target nerve populations or target neurons. Such sets of one or more stimulating contacts for use in stimulation are referred to herein as "stimulation channels." That is, a stimulation channel is made up of a single or multiple stimulating contacts.

In general, the stimulator unit 120 is configured to utilize the processed sound signals to generate electrical stimulation signals that are delivered to the recipient's cochlea via one or more stimulation channels. In this way, cochlear implant system 100 or 200 stimulates the recipient's auditory nerve cells, bypassing absent or defective hair cells that normally transduce acoustic vibrations into neural activity.

The human auditory system is composed of many structural components, some of which are connected extensively by bundles of nerve cells (neurons). Each nerve cell has a cell membrane which acts as a barrier to prevent intercellular fluid from mixing with extracellular fluid. The intercellular and extracellular fluids have different concentrations of ions, which leads to a difference in charge between the fluids. This difference in charge across the cell membrane is referred to herein as the membrane potential (Vm) of the nerve cell. Nerve cells use membrane potentials to transmit signals between different parts of the auditory system.

In nerve cells that are at rest (i.e., not transmitting a nerve signal) the membrane potential is referred to as the resting potential of the nerve cell. Upon receipt of a stimulus, the electrical properties of a nerve cell membrane are subjected to abrupt changes, referred to herein as a nerve action potential, or simply action potential. The action potential represents the transient depolarization and repolarization of the nerve cell membrane. The action potential causes electrical signal transmission along the conductive core (axon) of a nerve cell. Signals may be then transmitted along a group of nerve cells via such propagating action potentials.

Figure 2:
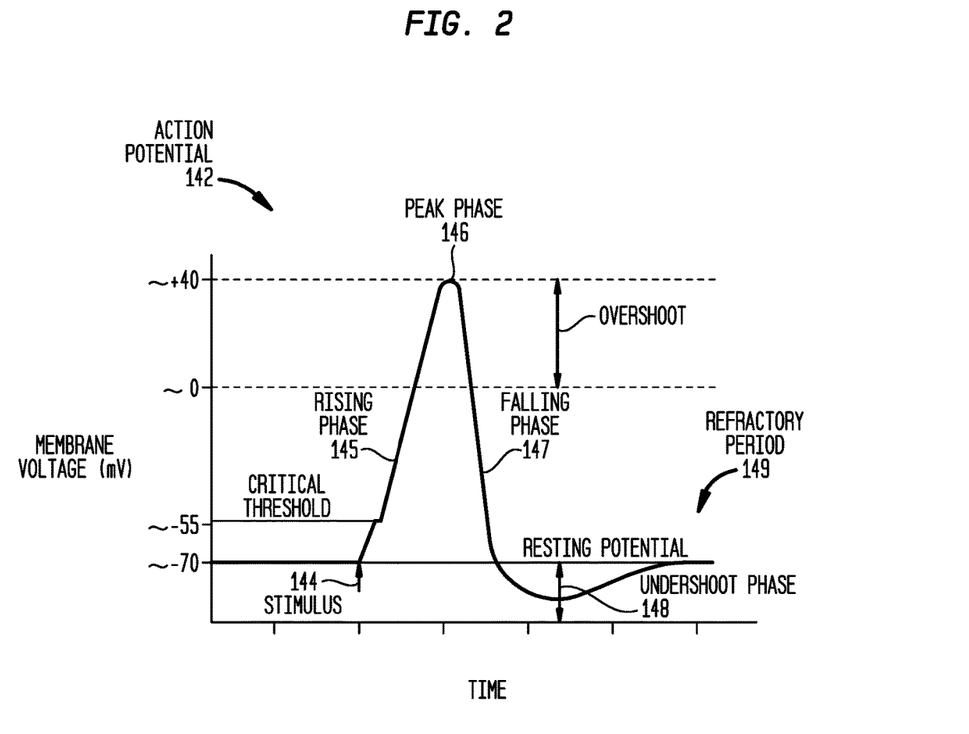
FIG. 2 is a graph illustrating various phases of an idealized action potential as the potential passes through a nerve cell.

FIG. 2 illustrates various phases of an idealized action potential 142 as the potential passes through a nerve cell. The action potential is presented as membrane voltage in millivolts (mV) versus time. The membrane voltages and times shown in FIG. 2 are for illustration purposes only and the actual values may vary depending on the individual. Prior to application of a stimulus 144 to the nerve cell, the resting potential of the nerve cell is approximately −70 mV. Stimulus 144 is applied at a first time. In normal hearing, this stimulus is provided by movement of the hair cells of the cochlea. Movement of these hair cells results in the release of a nerve impulse, sometimes referred to as neurotransmitter. In cochlear implants, the stimulus 144 is an electrical stimulation signal.

Following application of stimulus 144, the nerve cell begins to depolarize. Depolarization of the nerve cell refers to the fact that the voltage of the cell becomes more positive following stimulus 144. When the membrane of the nerve cell becomes depolarized beyond the cell's critical threshold, the nerve cell undergoes an action potential. This action potential is sometimes referred to as the "firing" of the nerve cell. As used herein, the critical threshold of a nerve cell, group of nerve cells, etc. refers to the threshold level at which the nerve cell, group of nerve cells, etc. will undergo an action potential. In the example illustrated in FIG. 2, the critical threshold level for firing of the nerve cell is approximately −50 mV. The critical threshold and other transitions may be different for various recipients and so the values provided in FIG. 2 are merely illustrative.

The course of the illustrative action potential in the nerve cell can be generally divided into five phases. These five phases are shown in FIG. 2 as a rising phase 145, a peak phase 146, a falling phase 147, an undershoot phase 148, and finally a refractory phase (period) 149. During rising phase 145, the membrane voltage continues to depolarize and the point at which depolarization ceases is shown as peak phase 146. In the example of FIG. 2, at this peak phase 146, the membrane voltage reaches a maximum value of approximately 40 mV.

Following peak phase 146, the action potential undergoes falling phase 147. During falling phase 147, the membrane voltage becomes increasingly more negative, sometimes referred to as hyperpolarization of the nerve cell. This hyperpolarization causes the membrane voltage to temporarily become more negatively charged than when the nerve cell is at rest. This phase is referred to as the undershoot phase 148 of action potential 142. Following this undershoot phase 148, there is a time period during which it is impossible or difficult for the nerve cells to fire. This time period is referred to as the refractory phase (period) 149.

Action potential 142 may travel along, for example the auditory nerve, without diminishing or fading out because the action potential is regenerated each nerve cell. This regeneration occurs because an action potential at one nerve cell raises the voltage at adjacent nerve cells. This induced rise in voltage depolarizes adjacent nerve cells thereby provoking a new action potential therein.

As noted above, the nerve cell must obtain a membrane voltage above a critical threshold before the nerve cell may fire. As such, conventional cochlear implant stimulation strategies stimulate nerve cells using discrete rectangular biphasic "constant-current pulses." As used herein, a constant-current pulse refers to a current pulse that is delivered to a recipient at a constant current (constant amplitude) for a period of time that is sufficient to raise the membrane voltage of the stimulated nerve cells above the critical threshold (i.e., each constant-current pulse has a time length and amplitude so as to cause the stimulated nerve cells to fire). A perceived loudness level of a constant current pulse is dependent upon the number of nerve cells that fire at around the same time. Increasing either the current amplitude or the time length of the pulse (or both) will result in a higher number of firing nerve cells and a higher perceived loudness. In other words, a single delivered current pulse has a constant amplitude that is applied to the nerve cells until the desired number of nerve cells fire.

To generate constant-current pulses, existing stimulation circuits utilize substantially high implant voltage supplies/rails and large current sources that inefficiently use energy through a partially open (partially conducting) transistor to regulate the constant current (i.e., linear regulation). Generating these high voltages results in efficiency losses and large off-chip components which increase the size of the stimulation circuit. In conventional cochlear implants, these current sources take up a large fraction of the integrated circuit (IC) surface area. In addition, the use of linear regulation to generate the constant current results in significant power consumption across the partially conducting transistors. For example, in a resistive device that includes transistors and other semiconductors, such as a conventional cochlear implant current source, the power dissipated is equal to the current flowing through the transistor multiplied by the voltage across the transistor.

Embodiments of the present invention are directed to techniques that eliminate the requirement to deliver constant-current pulses to evoke perception of sound signals. More specifically, as described further below, embodiments of the present invention are directed to stimulation techniques that utilize discrete sets/groups of micro-charge pulses, where each set of micro-charge pulses collectively cause the firing of a group of target nerve cells. That is, each of the micro-charge pulses alone delivers insufficient current to cause the firing of the target nerve cells, but the set of micro-charge pulses, when the micro-charge pulses are applied in sequence, is configured to cause the firing of the target nerve cells (i.e., when aggregated, the plurality of micro-charge pulses in a set cause firing of the target nerve cells).

A nerve cell functions so as to integrate the micro-charge pulses applied thereto (i.e., as a form of an electrical integrator). In other words, due to the short time lengths of the micro-charge pulses, and the frequency of the micro-charge pulses, the recipient does not perceive each of the individual micro-charge pulses, but instead perceives an average over time of the total integral current of the set of micro-charge pulses. Therefore, by delivering a series of micro-charge pulses to a group of nerve cells at a high frequency, the charge delivered by the collection of series of micro-charge pulses can cause the nerve cells to fire. The micro-charge pulses can, accordingly, avoid the need for large components to generate high voltages, as well as inefficiencies caused by the power consumption associated with linear regulation of constant current (e.g., through a partially conducting transistor). Future cochlear implants may require multiple current sources, thus reducing current source size and increasing their efficiency may become increasingly important.

Figure 3:
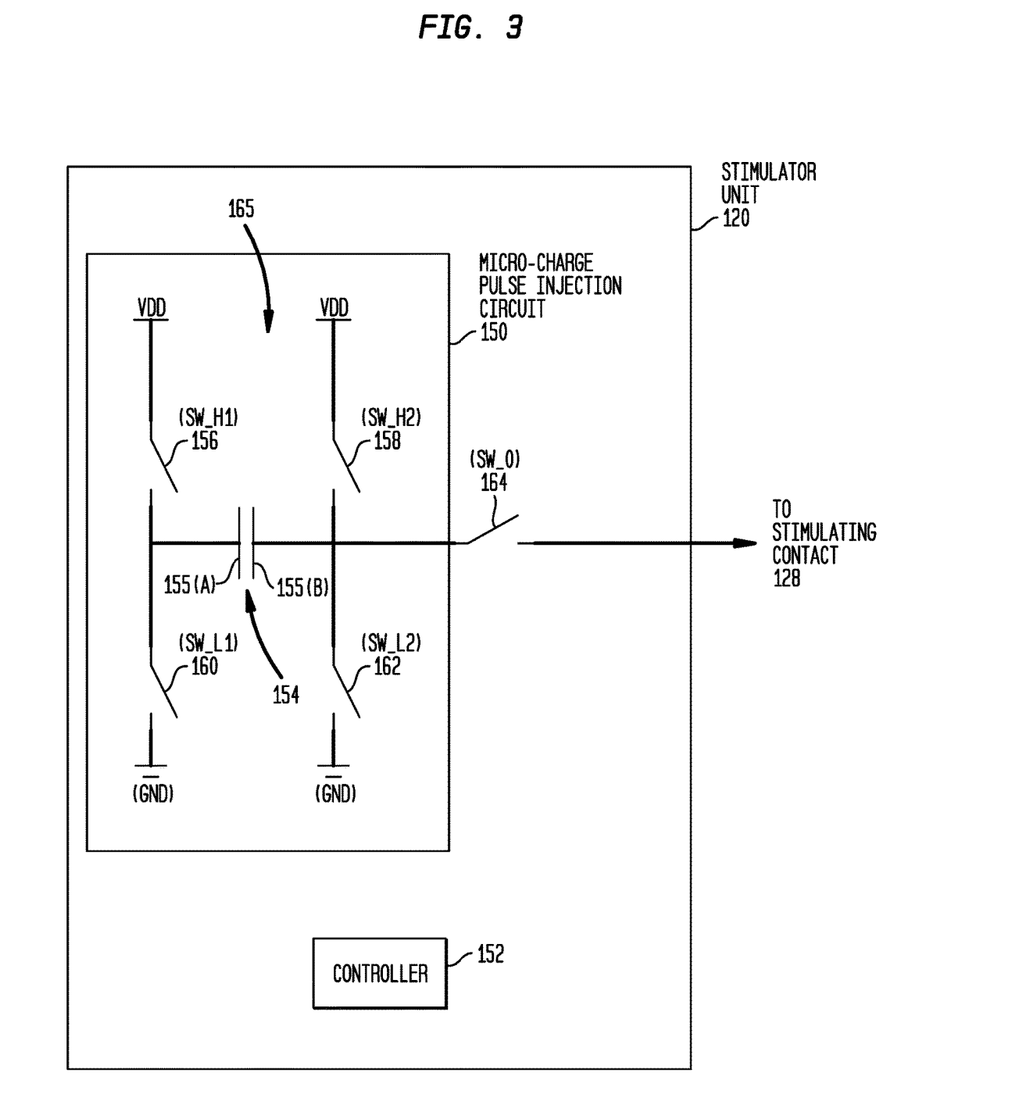
FIG. 3 is a schematic diagram illustrating a stimulator unit and a micro-charge pulse injection circuit in accordance with embodiments presented herein.

FIG. 3 is a schematic diagram illustrating one example arrangement for stimulator unit 120 in accordance with embodiments of the present invention. Stimulator unit 120 comprises a micro-charge pulse injection circuit 150, a switching circuit 164, and a controller 152. Micro-charge pulse injection circuit 150 includes a capacitor 154, a first switch 156 (SW_H1), a second switch 158 (SW_H2), a third switch 160 (SW_L1), and a fourth switch 162 (SW_L2). For ease of illustration, the switching circuit 164 is shown as a single switch (SW_O) and is sometimes referred to herein as the output switch or output switching circuit.

Switches 156, 158, 160, and 162 collectively form an H-Bridge (H Bridge) 165 around capacitor 154, thereby allowing a voltage to be applied across the capacitor in both directions. In particular, switch 156 is connected between the cochlear implant supply voltage, shown as Vdd, and a first terminal 155(A) of capacitor 154, while switch 158 is connected between the cochlear implant supply voltage and a second terminal 155(B) of the capacitor. Switch 160 is connected between ground (GND) (0 V) and the first terminal 155(A) of capacitor 154, while switch 162 is connected between ground and the second terminal 155(B) of the capacitor. Switch 164 is connected between the second terminal 155(B) of the capacitor 154 and at least one of the stimulating contacts 128 (FIG. 1A) implanted in the recipient's cochlea. As such, capacitor 154 is an H-Bridge activated capacitor that can source current into, or sink current from, (i.e., inject or withdraw charge into/from) the recipient's nerve cells.

Controller 152 controls the actuation of the switches in the micro-charge pulse injection circuit 150 (i.e., switches 156, 158, 160, and 162) and switch 164. However, for ease of illustration, connections between the controller 152 and the switches 156, 158, 160, 162, and 164 have been omitted from FIG. 3. Controller 152 may be implemented with digital logic gates in one or more application-specific integrated circuits (ASICs). However, in alternative arrangements, the controller 152 may include a processor and a memory with one or more software modules stored that are executable by the processor to control operation of the micro-charge pulse injection circuit 150.

Additionally, FIG. 3 illustrates the switches 156, 158, 160, 162, and 164 using simplified schematic representations. As described further below, the switches 156, 158, 160, 162, and 164 operate in both positive current and negative current contexts. As such, each of the switches 156, 158, 160, 162, and 164 are, in practice, switching circuits enabling operation with both positive and negative currents.

By opening and closing combinations of the switches 156, 158, 160, 162, and 164, with a proper timing, a plurality of pulses with different voltages may be created at the second terminal 155(B) of the capacitor 154 and the stimulating contact 128. For example, to generate a pulse at the connected stimulating contact 128 with a voltage that is equal to the cochlear implant supply voltage (i.e., Vdd), switches 158 and 160 are first closed, thereby allowing the second terminal 155(B) of capacitor 154 to charge to Vdd, while the first terminal 155(A) of the capacitor is connected to ground (i.e., capacitor 154 charges to Vdd). Subsequently, switch 158 is opened and switch 164 is closed to inject a pulse into the recipient's tissue via the stimulating contact 128. That is, since switch 164 is connected between the second terminal 155(B) of capacitor 154 and the stimulating contact 128, once switch 164 is closed the connected stimulating contact takes the voltage that is at the second terminal 155(B) of the capacitor (i.e., Vdd). In such examples, the voltage on the stimulating contact 128 is initially Vdd and will drop as current flows out of the capacitor 154 into the recipient's tissue. Current will continue to flow until switch 164 is opened.

Additionally, to generate a pulse at the connected stimulating contact 128 with a polarity opposite to that of the cochlear implant supply voltage (i.e., −Vdd), switches 156 and 162 are first closed, thereby allowing the first terminal 155(A) of capacitor 154 to charge to Vdd, while the second terminal 155(B) of the capacitor is connected to ground (i.e., capacitor 154 charges to Vdd, but with reverse polarity). Subsequently, switches 156 and 162 are opened and switches 160 and 164 are closed to inject a pulse into the recipient's tissue via the stimulating contact 128. That is, since switch 164 is connected between the second terminal 155(B) of capacitor 154 and the stimulating contact 128, once switch 164 is closed the stimulating contact takes the voltage that is at the second terminal 155(B) of the capacitor (i.e., −Vdd). The voltage on the stimulating contact 128 is initially −Vdd and will rise (towards 0 V/ground) as current flows into capacitor 154 from the recipient's tissue. Current will flow until switch 164 is opened.

To generate a pulse at the connected stimulating contact 128 with a voltage of two times Vdd (2×Vdd), switches 158 and 160 are first closed, thereby allowing the second terminal 155(B) of capacitor 154 to charge to Vdd, while the first terminal 155(A) of the capacitor is connected to ground (i.e., capacitor 154 charges to Vdd). If switches 158 and 160 are opened, and switch 156 is closed, then the first terminal 155(A) of capacitor 154 is held at a voltage of Vdd. However, since the capacitor 154 already has a voltage of Vdd across it, the second terminal 155(B) of capacitor 154 has a potential (voltage) of two times the cochlear implant supply voltage (i.e., has a voltage of 2×Vdd). If switch 164 is then closed, then the voltage of twice the implant supply voltage appears on the connected stimulating contact 128. The voltage on the stimulating contact 128 is initially 2×Vdd and will drop as current flows out of capacitor 154 into the recipient's tissue. Current will flow until switch 164 is opened.

As shown, both terminals of the charge storage capacitor 154 are switchable between ground and the cochlear implant supply voltage. This allows the generation of voltages that are higher than the implant supply voltage (i.e., the micro-charge pulse injection circuit 150 can generate pulses having voltages equal to the cochlear implant supply voltage, or multiples of the cochlear implant supply voltage from a single power supply). Additionally, by switching at a very high frequency (e.g., 1-10 megahertz (MHz)), the capacitor 154 may be relatively small (e.g., 20 picofarads (pF)). This enables the micro-charge pulse injection circuit 150 to be made sufficiently small so that it can be integrated on a single integrated circuit chip multiple times, thereby leading to the ability to simultaneously generate multiple sets of micro-charge pulses for delivery to different stimulating contacts.

Moreover, in accordance with the examples presented herein, switches 156, 158, 160, 162 and 164 operate only in either a "fully on" or "fully off" state (i.e., there are no partially conducting transistors). This has the advantage of minimizing the power lost across the circuit during operation because (other than the brief transient periods during switching), either the voltage across the switches, or the current through the switches, is substantially zero (i.e., power=current×voltage). This is in contrast to the transistors in existing implantable current sources in which the transistors operate in the linear region where they have both current flowing through them and voltage across them during operation and, accordingly, are dissipating power throughout the duration of the current pulse.

The stimulator unit 120 is configured to receive the processed sound signals and to use the processed sound signals to generate sets/clusters of micro-charge pulses for delivery to the recipient. Each set of micro-charge pulses comprises a plurality of pulses that are generated and delivered via the same stimulating contact in a relatively short period of time so as to initiate firing of a group of cochlea nerve cells and, accordingly, evoke perception of at least a portion of the processed sound signals. The micro-charge pulses are each generated, as described above with reference to FIG. 3, through selective actuation of H-Bridge 165.

For ease of illustration, FIG. 3 illustrates a single micro-charge pulse injection circuit 150 in stimulator unit 120. In such embodiments, switch 164 may be a switching circuit that selectively connects the micro-charge pulse injection circuit 150 to a plurality of different stimulating contacts at different times. As such, the single micro-charge pulse injection circuit 150 may be utilized as a current source for different stimulating contacts. However, as described further below, it is to be appreciated that in alternative embodiments, stimulator unit 120 may include multiple micro-charge pulse injection circuits that are each selectively connectable to one or more stimulating contacts.

Figure 4:
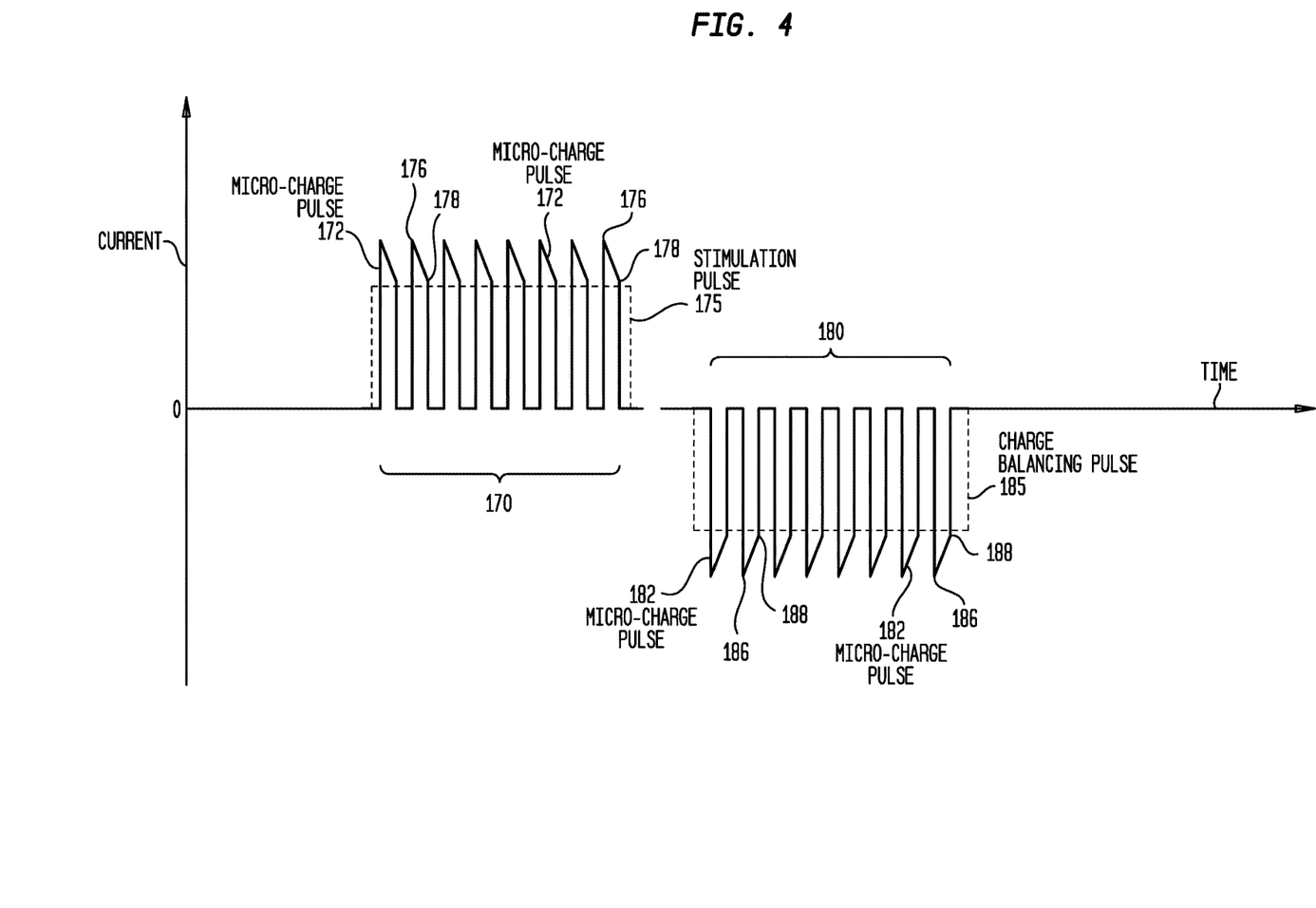
FIG. 4 is a timing diagram illustrating micro-charge pulses in accordance with embodiments presented herein.

FIG. 4 is a timing diagram illustrating, in terms of current amplitude (e.g., milliamps (mA)) versus time, two (2) sets of micro-charge pulses generated by micro-charge pulse injection circuit 150 in accordance with embodiments presented herein. More particularly, shown in FIG. 4 is a first micro-charge pulse set 170 formed by a plurality of individual micro-charge pulses 172. The first micro-charge pulse set 170 includes eight (8) micro-charge pulses 172 generated at a voltage of Vdd, as described above with reference to H-Bridge 165.

Each micro-charge pulse 172 includes a peak 176 that represents the maximum current flow into the recipient's tissue during the corresponding micro-charge pulse. The peak 176 of the current flow is at the instant when switch 164 is first closed on that the capacitor 154, which was previously charged to Vdd, is first discharged into the recipient's tissue. Each micro-charge pulse 172 also includes a cut-off 178 that represents the minimum current flow into the recipient's tissue i.e., the current flow immediately before switch 164 is opened). As such, each micro-charge pulse 172 has a generally declining amount of current flowing into the recipient's tissue with respect to time.

As noted above, the recipient's cochlea tissue functions so as to integrate the micro-charge pulses 172. That is, due to the short time length of each of the micro-charge pulses and the frequency at which the micro-charge pulses are delivered within a discrete time period, the recipient does not perceive each of the individual micro-pulses. Instead, the recipient perceives an average over time of the total integral current. The current that is actually perceived by the recipient is shown in FIG. 4 as "stimulation pulse" 175. The stimulation pulse 175 is shown using a broken line in order to represent that the stimulation pulse is not a delivered current pulse, but is instead the perceived effect of the set of micro-charge pulses 172.

In summary, FIG. 4 illustrates that the micro-charge pulses 172 within set 170, when delivered in sequence to cochlea nerve cells of the recipient, collectively (i.e., in aggregate) cause the recipient to perceive a current having an amplitude that is a time average of the total integral current delivered by the micro-charge stimulation pulses. This enables the micro-charge pulses 172 within set 170, when delivered in sequence to cochlea nerve cells of the recipient, to collectively evoke perception of at least a portion of a sound signal.

FIG. 4 also illustrates a second micro-charge pulse set 180 formed by a plurality of individual micro-charge pulses 182. The second micro-charge pulse set 180 includes eight (8) micro-charge pulses 182 generated at a voltage of −Vdd, as described above with reference to H-Bridge 165.

Each micro-charge pulse 182 includes a peak 186 that represents the maximum current flow from recipient's tissue into the capacitor 154 during the corresponding micro-charge pulse. The peak 186 of the current flow is at the instant when the switch 164 is first closed so that current flows in capacitor 154. Each micro-charge pulse 182 also includes a cut-off 188 that represents the minimum current flow into the capacitor 154 (i.e., the current flow immediately before switch 164 is opened). As such, each micro-charge pulse 182 has a generally declining amount of current flowing into the capacitor 154 with respect to time.

Similar to micro-charge pulses 172, the recipient's cochlea tissue functions to integrate the micro-charge pulses 182 (i.e., the recipient does not perceive each the individual micro-pulses 182, but instead perceives an average over time of the total integral current). The current that is actually perceived by the recipient is shown in FIG. 4 as "charge balancing pulse" 185 (i.e., the charge balancing pulse is evoked through the sequential aggregate delivery of the micro-charge pulses 182). The charge balancing pulse 185 is shown using a broken line in order to represent that the charge balancing pulse is not a delivered current pulse, but is instead the perceived effect of the set of micro-charge pulses 182.

FIG. 4 illustrates two sequential sets of micro-charge pulses generated with opposite polarities, where the first micro-charge pulse set 170 injects charge into the recipient's tissue and the second micro-charge pulse set 180 removes charge from the tissue. As such, the combination of set 170 and set 180 collectively represent a form of biphasic current stimulation. Biphasic stimulation is important so as to enable charging balancing in the cochlea tissue.

As detailed above, the micro-charge pulses 172 are generated by releasing charge from capacitor 154, while micro-charge pulses 182 are generated by pulling charge into capacitor 154, thereby generating different voltages at the connected stimulating contact 128. Assuming for ease of illustration that the stimulating contacts 128 and cochlea tissue are primarily resistive to ground, the voltage pulses and current pulses have the same general shape. In practice, the stimulating contacts 128 and cochlea tissue have a more complex collective impedance. However, even accounting for a more complex collective impedance, the micro-charge pulses would have a similar shape pulse that starts with an initially high current that drops over the course of the micro-charge pulse. However, it is to be appreciated that the current does not necessarily drop in a linear manner.

The amount of stimulation charge delivered in a micro-charge pulse set is controlled by (1) varying the number of micro-charge pulses in a set, (2) varying the time length of each micro-charge pulse (i.e., varying how long the capacitor 154 is connected to the stimulating contact per cycle and therefore how much the capacitor discharges per cycle), and (3) varying the initial charge voltage per cycle (1×, 2× or 3× the cochlear implant supply voltage). It is noted that a voltage of 3× the cochlear implant supply voltage is achieved by driving one circuit with +2× of the supply voltage and driving the reference electrode with −1× of the supply voltage.

As described further below with reference to FIG. 6, the amount of stimulation charge delivered in a micro-charge pulse set may also be controlled by varying the size of the charge storage capacitor by switching in or out extra capacitors in parallel to capacitor 154. In addition, the cochlear implant supply voltage (VDD) can be varied to achieve a change in the effective current.

Figure 5:
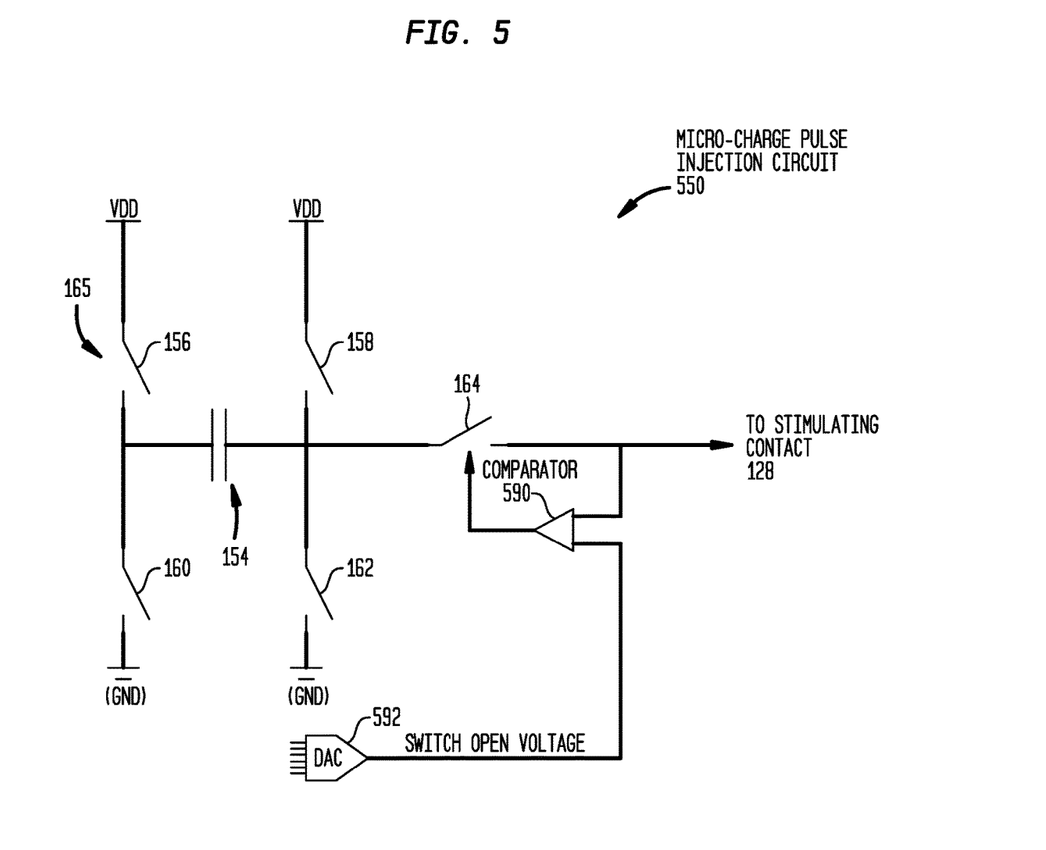
FIG. 5 is a schematic diagram illustrating another micro-charge pulse injection circuit in accordance with embodiments presented herein.

FIG. 5 is a schematic diagram illustrating a micro-charge pulse injection circuit 550 that is configured for additional charge delivery control in accordance with embodiments of the present invention. Similar to the arrangement of FIG. 3, micro-charge pulse injection circuit 550 comprises capacitor 154 and H-Bridge 165 formed by switches 156, 158, 160, and 162. However, in the example of FIG. 5, micro-charge pulse injection circuit 550 also includes a comparator 590 and a digital-to-analog converter (DAC) 592.

In operation, the DAC 592 and comparator 590 control the output voltage at which output switch 164 opens such that each micro-charge pulse sends or sinks a controlled (selected) amount of charge (Q) (i.e., control the amount of charge delivered per cycle). More specifically, the DAC 590 applies a selected voltage to a first input of the comparator 590, while a second input of the comparator is connected to the output of switch 164. As a result, the comparator 590 is configured to continually compare the voltage at the output of switch 164, which is the voltage delivered to the connected stimulating contact 128, to the selected voltage applied by the DAC. The comparator 590 operates to open switch 164 when the voltage at the output of switch 164 falls below the applied DAC voltage.

The controllable charge Q is related to the capacitance and the change in voltage (i.e., Q=capacitance×ΔV), and current=charge/time and therefore, a controllable equivalent current may be delivered. The equivalent current is controlled using both the DAC voltage and the number of delivered micro-pulses per set (i.e., equivalent current=total charge/total time). Stated differently, current may be defined as charge divided by time. If capacitor 154 discharges N times, where N equals the number of micro-charge pulses, and the amount of charge per micro-charge pulse is Q, then the total charge delivered with a set of micro-charge pulses is N times Q. This total delivered charge, when divided by the time over which the N micro-charge pulses are delivered, provides the current delivered with each set of micro-charge pulses. Therefore, by controlling the switch 164 to open at a certain voltage, the average current delivered over a set of micro-charge pulses is controlled (i.e., the comparator 590 opens switch 164 at selected voltage at which it is known that a fixed charge Q has been removed from, or added to, the capacitor).

The embodiment of FIG. 5 may simplify the control logic (controller) when compared to the example of FIG. 3 in that the control logic only needs to control the closing of switch 164, while the comparator 590 and DAC 592 control the opening of the switch 164.

In the embodiment of FIG. 5, the comparator 590 and DAC 592 each operate on both the positive and negative pulses. It is to be appreciated that other embodiments may utilize two comparators and two DACs, where one comparator and one DAC operate on positive pulses and the other comparator and other DAC operate on negative pulses.

Figure 6:
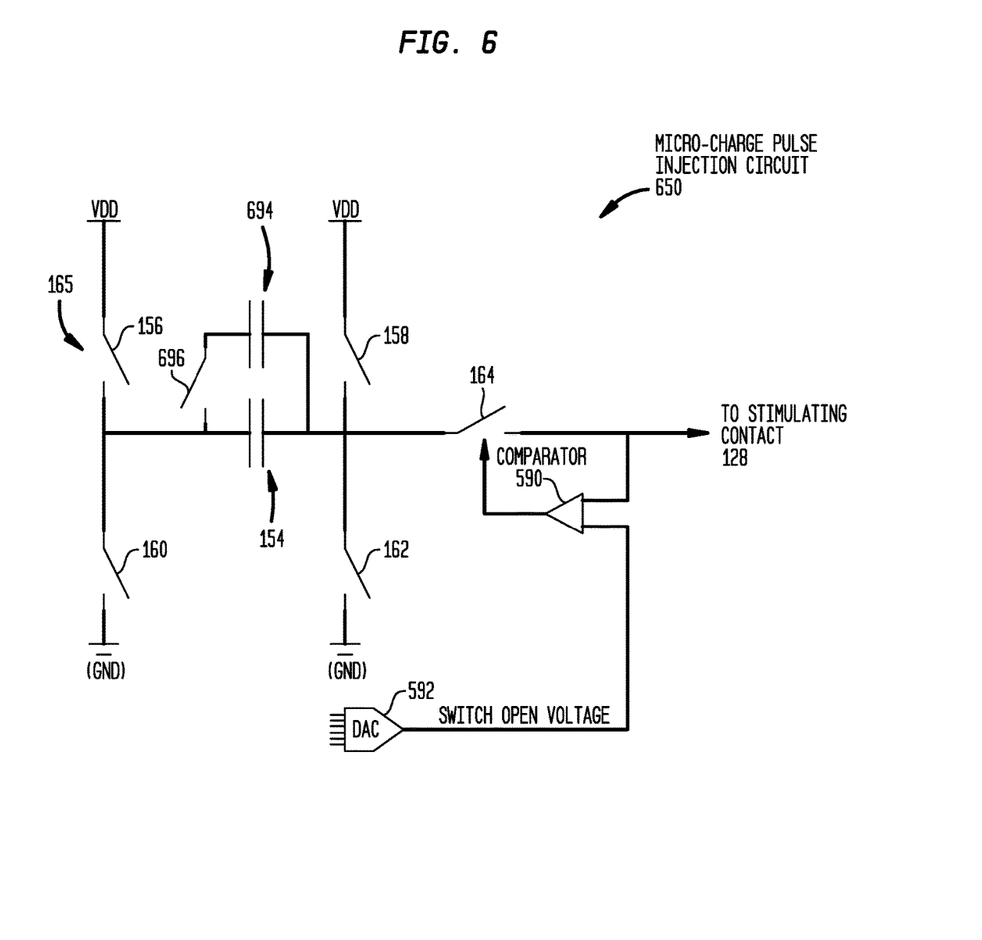
FIG. 6 is a schematic diagram illustrating another micro-charge pulse injection circuit in accordance with embodiments presented herein.

FIG. 6 is a schematic diagram illustrating an example arrangement for a micro-charge pulse injection circuit 650 in accordance with further embodiments of the present invention. Similar to the arrangement of FIG. 5, micro-charge pulse injection circuit 650 comprises comparator 590, DAC 592, capacitor 154, and H-Bridge 165 formed by switches 156, 158, 160, and 162. However, in the example of FIG. 6, micro-charge pulse injection circuit 650 also includes a second capacitor 694 that is connectable in parallel with capacitor 154 using an additional switch 696.

FIG. 6 illustrates an example arrangement in which multiple capacitors could be used to vary the amount of delivered charge. For example, in circumstances in which the delivered charge should be lower, capacitor 154 may be used alone (i.e., switch 696 is open so that capacitor 694 is disconnected from the circuit). However, circumstances in which the delivered charge should be higher, switch 696 is closed to connect capacitor 694 in parallel with capacitor 154. When capacitor 694 is connected in parallel with capacitor 154, both capacitors may be charged or discharged by the H-Bridge 165, thereby enabling the sourcing or sinking of additional current with each micro-charge pulse.

For ease of illustration, embodiments of the present invention have been described with reference to the use of a stimulator unit with a single micro-charge pulse injection circuit. However, as noted above, certain embodiments of the present invention may include multiple micro-charge pulse injection circuits incorporated in a single implantable medical device. Such embodiments provide the ability to simultaneously generate multiple sets of micro-charge pulses for delivery to different stimulating contacts.

Figure 7:
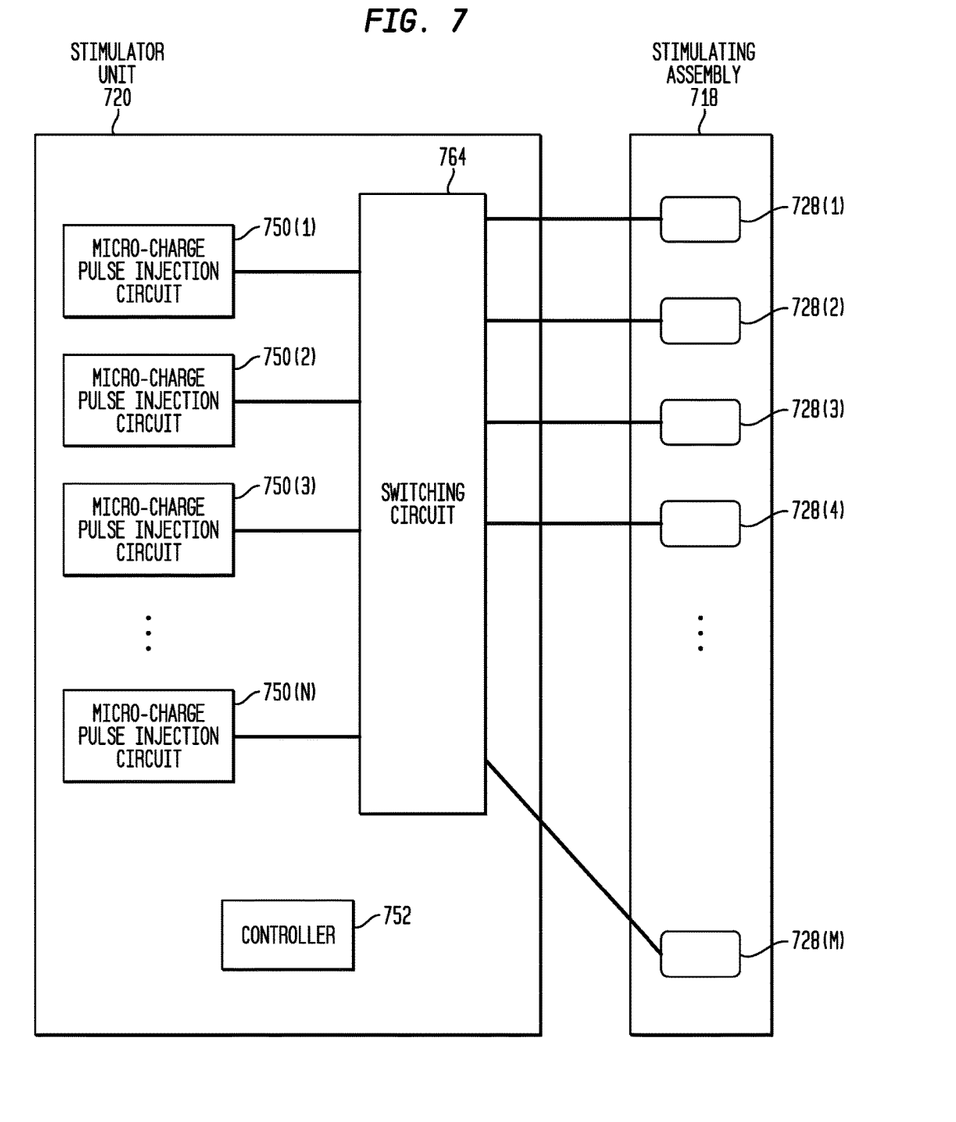
FIG. 7 is a schematic diagram illustrating a stimulator unit in accordance with embodiments presented herein.

For example, FIG. 7 is a block diagram illustrating a stimulator unit 720 that includes multiple micro-charge pulse injection circuits 750(1)-750(N). The stimulator unit 720 includes a switching circuit 764 that enables the micro-charge pulse injection circuits 750(1)-750(N) to be selectively connected to one or more stimulating contacts 728(1)-728(M) in a stimulating assembly 718. Operation of the micro-charge pulse injection circuits 750(1)-750(N) and switching circuit 764 is controlled by at least one controller 752. The controller 752 may be implemented with digital logic gates in one or more ASICs or may include one or more processors and one or more memories with one or more software modules that are executable by the processor(s) to control operation of the micro-charge pulse injection circuits 750(1)-750(N) and switching circuit 764.

Figure 8:
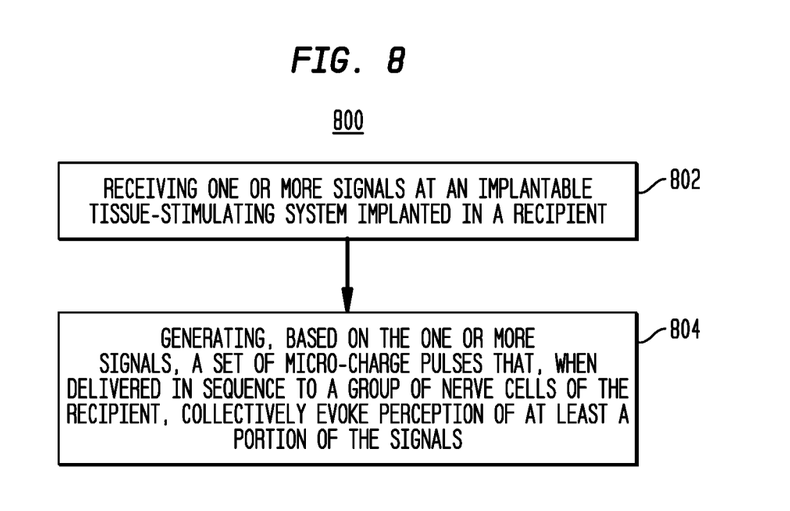
FIG. 8 is a flowchart of a method in accordance with embodiments presented herein.

FIG. 8 is a flowchart of a method 800 in accordance with embodiments presented herein. Method 800 begins at 802 where one or more sound signals are received at a stimulating auditory system. At 804, a stimulator unit generates, based on the one or more sound signals, a set of micro-charge pulses that, when delivered in sequence to a group of nerve cells of the recipient, collectively evoke perception of at least a portion of the sound signals.

Embodiments of the present invention have been described with reference to an H-Bridge circuit operating with a capacitor to inject micro-charge pulses into a recipient's tissue. In an alternative arrangement, the capacitor can be replaced with an inductor, and the switch timing changed. This results in very brief high voltage pulses at the stimulating contacts from only a single implant voltage (Vdd) supply.

In certain examples, the techniques presented herein provide an efficient mechanism for generating different voltages from a single implant supply voltage (Vdd). For example, a micro-charge pulse injection circuit in accordance with embodiments presented herein may utilize a single +5V supply to generate stimulation pulses of +10V and −5V, i.e. peak-to-peak 15V. As such, no high voltage supply is needed to power the current source.

In addition, by eliminating the requirement for linear regulation of current, the micro-charge pulse injection circuit is relatively small, efficient, and lower power. The techniques presented herein also enable control of the amount of current delivered with each set of micro-charge stimulation pulses by adjusting both the number of capacitor charge dump cycles and the amount of time the output switch is closed (e.g., using the DAC output), thereby providing high current resolution.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A method, comprising:
   receiving one or more sound signals via at least one sound input element of a stimulating auditory system implanted in a recipient; and
   at a sound processor of the stimulating auditory system, generating processed sound signals representative of the one or more sound signals;
   at a stimulator unit of the stimulating auditory system, generating, based on the processed sound signals, a first set of positive polarity micro-charge pulses;
   delivering the first set of positive polarity micro-charge pulses in sequence to a group of nerve cells of the recipient via a single stimulation channel, wherein the first set of positive polarity micro-charge pulses collectively evoke perception of at least a portion of the processed sound signals, wherein each micro-charge pulse is generated by the discharge of a single capacitor having a sufficiently small size such that each micro-charge pulse in the first set of micro-charge pulses is delivered at a peak current that delivers insufficient charge alone to activate the group of nerve cells;
   at the stimulator unit, generating a second set of micro-charge pulses each having a negative polarity; and
   following delivery of the first set of micro-charge pulses, delivering the second set of negative polarity micro-charge pulses in sequence to the group of nerve cells of the recipient to withdraw a charge associated with the first set of micro-charge pulses from the group of nerve cells.

2. The method of claim 1, wherein generating the first set of micro-charge pulses comprises:
   generating the micro-pulses with time durations and at a frequency to cause the recipient to perceive an average over time of a total integral current of the set of micro-charge pulses.

3. The method of claim 1, further comprising:
   generating each micro-charge pulse in the first set of micro-charge pulses with a switched capacitor circuit formed by a plurality of switches configured to be selectively activated to connect first and second sides of the capacitor to at least one of a supply voltage and a ground.

4. The method of claim 3, wherein the stimulating auditory system comprises a plurality of stimulation channels terminating in one or more stimulating contacts, and wherein the method further comprises:
   delivering each micro-charge pulse in the set of micro-charge pulses to the group of nerve cells via at least one switching circuit connected between the capacitor and at least one stimulating contact.

5. The method of claim 4, further comprising:
   monitoring a voltage at an output of the switching circuit; and
   determining, based on the voltage at the output of the switching circuit, when a predetermined amount of charge has been delivered by a micro-charge pulse; and
   opening the switching circuit when the predetermined amount of charge has been delivered by the micro-charge pulse.

6. The method of claim 1, wherein the stimulating auditory system comprises a plurality of stimulation channels each terminating in one or more stimulating contacts.

7. The method of claim 6, wherein the first set of micro-charge pulses represent a first portion of the one or more sound signals, and wherein the method further comprises:
   delivering the first set of micro-charge pulses to the recipient via a first stimulation channel to evoke perception of the first portion of the one or more sound signals;
   generating a third set of micro-charge pulses representative of a second portion of the one or more sound signals; and
   delivering the third set of micro-charge pulses to the recipient via a second stimulation channel to evoke perception of the second portion of the one or more sound signals.

8. The method of claim 7, further comprising:
   varying between the first and third sets of micro-charge pulses one or more of the number of micro-charge pulses in a set, the time length of each micro-charge pulse in a set, and an initial charge voltage of each micro-charge pulse in a set.

9. A method, comprising:
   generating, at a sound processor of a stimulating auditory system, processed sound signals;
   generating, at a micro-charge pulse injection circuit implanted in a recipient, a first plurality of micro-charge pulses based on the processed sound signals;
   delivering, via a switching circuit implanted in the recipient, the first plurality of micro-charge pulses to a group of nerve cells of the recipient in sequence via a stimulation channel so as to evoke perception of at least a portion of the processed sound signals, wherein each of the first plurality of micro-charge pulses has a first polarity and is generated by the discharge of a single capacitor having a sufficiently small size such that each micro-charge pulse delivers insufficient charge alone to activate the group of nerve cells;

generating, at the micro-charge pulse injection circuit implanted in a recipient, a second plurality of micro-charge pulses; and following delivery of the first plurality of micro-charge pulses, delivering, via the switching circuit implanted in the recipient, the second plurality of micro-charge pulses to the group of nerve cells of the recipient in sequence to withdraw a charge associated with the first plurality of micro-charge pulses from the group of nerve cells.

10. The method of claim 9, wherein generating the first plurality of micro-charge pulses comprises:

generating the first plurality of micro-pulses with time durations and at a frequency to cause the recipient to perceive an average over time of a total integral current of the set of micro-charge pulses.

11. The method of claim 9, wherein the micro-charge pulse injection circuit comprises a switched capacitor circuit formed by a plurality of switches configured to be selectively activated to connect first and second sides of the capacitor to at least one of a supply voltage and a ground.

12. The method of claim 9, further comprising:

monitoring a voltage at an output of the switching circuit; and determining, based on the voltage at the output of the switching circuit, when a predetermined amount of charge has been delivered by at least one micro-charge pulse in the first plurality of micro-charge pulses; and opening the switching circuit when the predetermined amount of charge has been delivered by the at least one micro-charge pulse.

13. The method of claim 9, wherein the stimulating auditory system comprises a plurality of stimulation channels each terminating in one or more stimulating contacts.

14. The method of claim 13, wherein the first plurality of micro-charge pulses are representative of a first portion of the processed sound signals, and wherein the method further comprises:

generating a third plurality of micro-charge pulses representative of a second of the processed sound signals;

delivering the first plurality of micro-charge pulses to the recipient via a first stimulation channel to evoke perception of the first portion of the one or more sound signals; and delivering the third plurality of micro-charge pulses to the recipient via a second stimulation channel to evoke perception of the second portion of the one or more sound signals.

15. The method of claim 14, further comprising:

varying between the first and third plurality of micro-charge pulses one or more of the number of micro-charge pulses, the time length of each micro-charge pulse, and an initial charge voltage of each micro-charge pulse.

16. The method of claim 13, delivering both the first and second plurality of micro-charge pulses to the group of nerve cells via a single stimulation channel.

17. A stimulating auditory system, comprising:

at least one sound input element configured to receive one or more sound signals;

a sound processor configured to generate processed sound signals representative of the one or more sound signals; and an implantable stimulator unit configured to:

generate, based on the processed sound signals, a first set of micro-charge pulses each having a positive polarity;

deliver the first set of micro-charge pulses to a group nerve cells of a recipient via a single stimulation channel, wherein the first set of micro-charge pulses collectively activate the group of nerve cells to evoke perception of a portion of the processed sound signals, and wherein each micro-charge pulse is generated by the discharge of a single capacitor having a sufficiently small size such that each micro-charge pulse in the first set of micro-charge pulses delivers insufficient charge alone to activate the group of nerve cells;

generate a second set of micro-charge pulses each having a negative polarity; and following delivery of the first set of micro-charge pulses, deliver the second set of micro-charge pulses to the recipient to collectively withdraw a charge associated with the first set of micro-charge pulses from the group of nerve cells.

18. The stimulating auditory system of claim 17, wherein the stimulator unit comprises:

at least one micro-charge pulse injection circuit that includes a plurality of switches configured to be selectively activated to connect first and second sides of the capacitor to at least one of a supply voltage and a ground;

a controller configured to actuate the plurality of switches to selectively connect the first and second sides of the capacitor to at least one of the supply voltage and the ground to generate each of the micro-charge pulses in the first and second sets of micro-charge pulses; and an output switching circuit configured to connect the at least one micro-charge pulse injection circuit to one or more stimulating contacts.

19. The stimulating auditory system of claim 18, wherein the at least one micro-charge pulse injection circuit comprises:

at least one comparator having a first input connected to an output of the output switching circuit such that the first input of the comparator has an input value that is the same as the voltage at the output of the output switching circuit; and at least one digital-to-analog converter (DAC) configured to apply a predetermined voltage to a second input of the comparator, wherein the comparator is configured to open the switching circuit when the voltage at the output of the output switching circuit is equal to the predetermined voltage.

20. The stimulating auditory system of claim 18, wherein the at least one micro-charge pulse injection circuit comprises a plurality of micro-charge pulse injection circuits that each includes a respective plurality of switches configured to be selectively activated to connect first and second sides of one or more capacitors to at least one of the supply voltage and the ground.

21. The stimulating auditory system of claim 17, further comprising a plurality of stimulating contacts configured to be positioned adjacent to nerve cells.

\* \* \* \* \*